United States Patent

Greco

Patent Number: 5,081,257
Date of Patent: Jan. 14, 1992

[54] NEW POLYOXAZOLIDINES, PROCESS FOR PREPARING THEM AND USE THEREOF

[75] Inventor: Alberto Greco, Dresano, Italy

[73] Assignee: Enichem Synthesis S.p.A., Palermo, Italy

[21] Appl. No.: 461,382

[22] Filed: Jan. 5, 1990

[30] Foreign Application Priority Data

Jan. 13, 1989 [IT] Italy ............................... 19089 A/89

[51] Int. Cl.$^5$ ............................................ C07D 263/04
[52] U.S. Cl. .................................................... 548/215
[58] Field of Search ........................................ 548/215

[56] References Cited

U.S. PATENT DOCUMENTS 4,504,647 3/1985 Zabel et al. ...................... 548/215

Primary Examiner—Maurice J. Welsh
Assistant Examiner—Rachel Johnson
Attorney, Agent, or Firm—Hedman, Gibson, Costigan & Hoare

[57] ABSTRACT

New polyoxazolidines can be defined by means of the general formula:

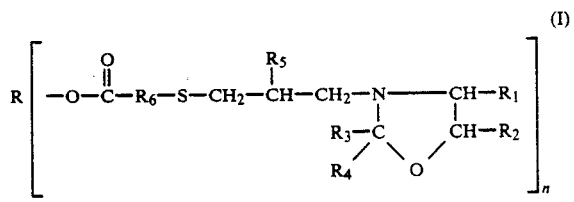

wherein $R$, $R_1$, $R_2$, $R_3$, $R_4$, $R_5$, $R_6$ and n have the meaning as reported in the specification. These polyoxazolidines are useful as crosslinking agents for moisture-hardening systems on the basis of polyisocyanates, acrylate polymers and polyepoxides, in compositions for coatings, sealant compositions and adhesive compositions.

3 Claims, No Drawings

NEW POLYOXAZOLIDINES, PROCESS FOR PREPARING THEM AND USE THEREOF

The present invention relates to new polyoxazolidines, to the process for preparing them and to their use as crosslinking agents for moisture-hardening systems on the basis of polyisocyanates, acrylate polymers and polyepoxides, in compositions for coatings, sealant compositions and adhesive compositions.

In U.S. Pat. No. 3,743,626, the use is disclosed of some polyoxazolidines as hardening agents, under room conditions of temperature and humidity, for adhesives based on polyisocyanates, of both aromatic and aliphatic nature. As disclosed in U.S. Pat. No. 4,138,545, such polyoxazolidines can be obtained by means of the reaction of an oxazolidine (A):

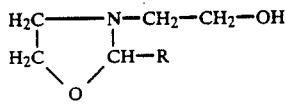

with lower alkyl esters of dicarboxy acids or of polycarboxy acids, by operating under transesterification conditions; or by means of the reaction of an oxazolidine (B):

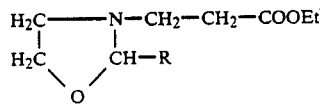

with a glycol or a polyol, still operating under transesterification conditions. The oxazolidines (B) are obtained in their turn by means of the addition of aldehydes to an addition product obtained from ethanolamine and an alkyl acrylate.

Such transesterification reactions require such catalysts as the alkali metal alkoxides or organometallic compounds (such as, e.g., titanium alkoxides), which are not easily eliminated from the reaction medium and endanger the stability of the polyisocyanates. Furthermore, drastic reaction conditions are required for the treansesterification to be completed, with the products obtained being consequently damaged.

Belgian patent No. 865,893 discloses the use of some polyoxazolidines in sealant compositions on polyisocyanate basis. As disclosed in Belgian patent No. 833,821, these polyoxazolidines can be obtained by means of the addition of oxazolidine (A) to polyisocyanates. These products are affected by the disadvantages deriving from the cost of polyisocyanates. Furthermore, due to the formation of urethanes in their synthesis, these products have unacceptably high values of viscosity, in particular when non-aliphatic diisocyanates, or, in general, polyisocyanates, are used.

European patent application publ. No. 288,935 discloses the use of polyoxazolidines as crosslinking agents in putties based on polyisocyanates, crosslinking under room conditions of humidity. In order to produce these polyoxazolidines, bis-(alkanolamines) (C):

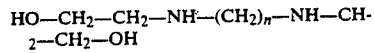

are used as the starting products.

The synthesis of such alkanolamines, by starting from amines and ethylene oxide, in not very selective. Furthermore, the need exists for such reaction products to be separated from the reaction mass, under conditions of high temperature and of high vacuum. The distillation is required by the need of eliminating the tertiary amines (i.e., the tri- and poly-alkanolamines) which, when added to the polyisocyanate systems, reduce the useful life thereof, owing to phenomena of premature crosslinking, caused by interactions of chemical nature, (alkanols), as well as by catalytic actions (the tertiary nitrogen).

U.S. Pat. No. 4,296,225 discloses the incorporation of polyoxazolidines as latent crosslinking systems, in polyvinylic systems, in the preparation of polyvinyl emulsions. In this case, the oxazolidine is introduced as a methacrylate of hydroxyalkyloxazolidine, or as a component in polyurethanic paints with a high content of solid matter. The principle is of the introduction of the oxazolidinic moiety into a polyacrylate, which is made possible by means of the use of a vinyl-oxazolidine, capable of copolymerizing to a variable extent with the acrylic monomers. In any case, the oxazolidinic equivalent is not high and the polymers are solids, or excessively viscous liquids, so that the need arises of dispersing them in water, or of dissolving them in an organic solvent.

The purpose of the present invention is a new class of polyoxazolidines which makes it possible the drawbacks which affect the prior art, to be overcome. In particular, according to the present invention a novel class of polyoxazolidines were found, which can be prepared in a simple and advantageous way, and which are useful as crosslinking agents in moisture-hardening systems on the basis of polyisocyanates, acrylate polymers or polyepoxides, for application in those cases in which a good resistance to heat, a good chemical resistance and a good ageing resistance is required, in such application sectors as the coatings, the sealants and the adhesives.

In accordance therewith, according to a first aspect thereof, the present invention relates to new polyoxazolidines which can be defined by means of the general formula:

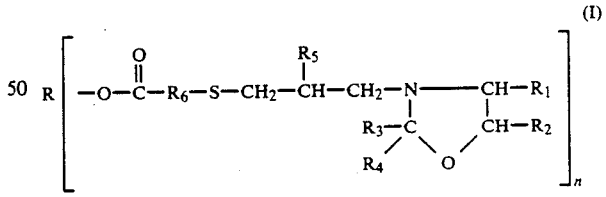

wherein:

R is an alkylenic radical containing from 2 to 12 carbon atoms, or a cycloalkylenic radical;

$R_1$ and $R_2$, which can be either equal to, or different from, each other, represent the hydrogen atom, an alkyl radical with a straight or branched chain, containing from 1 to 6 carbon atoms, or an aryl radical;

$R_3$ and $R_4$, which can be either equal to, or different from, each other, represent the hydrogen atom, an alkyl radical with a straight or branched chain, containing from 1 to 6 carbon atoms, a cycloalkyl radical, or an aryl radical;

$R_5$ represents the hydrogen atom or the methyl radical;

$R_6$ represents the methylene radical —$CH_2$— or the ethylidene radical —$CH_2$—$CH_2$—, and n represent and integer comprised within the range of from 2 to 10.

In the preferred form of practical embodiment,

R is an alkylenic radical containing from 2 to 6 carbon atoms;

$R_1$ and $R_2$ represent the hydrogen atom;

$R_3$ and $R_4$ represent, independently from each other, an alkyl radical with a straight or branched chain, containing from 1 to 4 carbon atoms; or either of $R_3$ and $R_4$ represents a hydrogen atom, and the other one represents an alkyl radical with a straight or branched chain, containing from 1 to 4 carbon atoms;

$R_5$ represents the hydrogen atom or the methyl radical;

$R_6$ represents the methylene radical or the ethylidene radical; and n represent an integer comprised within the range of from 2 to 6.

The polyoxazolidines according to the present invention can be obtained as shown in the reaction scheme reported in the following, in which, in the formulae, R, $R_1$, $R_2$, $R_3$, $R_4$, $R_5$, $R_6$ and n have the hereinabove specified meaning.

More particularly, by referring to such a reaction scheme, (meth)allyl-amine (II) is reacted first with alkylene oxide (III) in order to yield N-(meth)-allyl-alkanol-amine (IV).

The preferred alkylene oxide (III) is ethylene oxide.

The reaction is exothermic an proceeds easily at a temperature comprised within the range of from 0° to 120° C., with a ratio of (meth)allyl-amine to the alkylene oxide being adopted, which is comprised within the range of from 1:1 to 10:1. However, the reaction should advantageously be carried out in the presence of an excess of (meth)allyl-amine, in order to substantially prevent the further addition of alkylene oxide to N-(meth)allyl-alkanol-amine, which leads to the formation of the undesired product N-dialkanolamine.

REACTION SCHEME

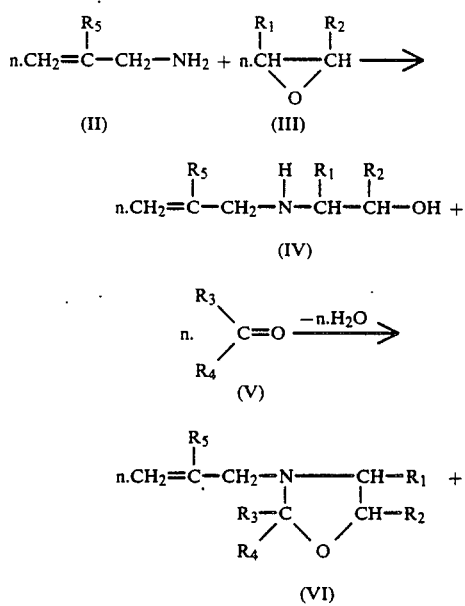

-continued

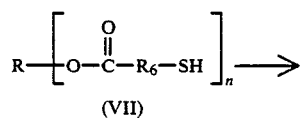

(VII)

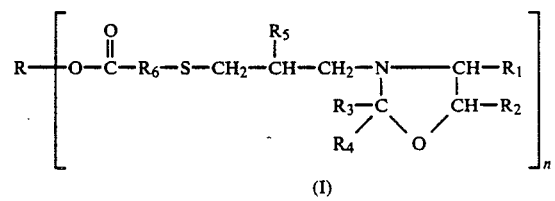

(I)

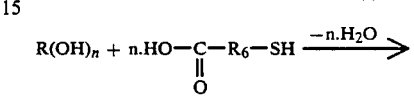

(VIII)   (IX)

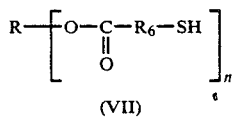

(VII)

By operating under the above reported conditions, the selectivity to the useful reaction product can reach values as high as 95%, and the so obtained reaction products are suitably submitted to a rectification in order to recover the excess of (meth)allylamine and to eliminate any traces of N-dialkanol-amine byproduct.

The N-(meth)-allyl-alkanol-amine (IV) is then reacted with the aldehyde or ketone (V) in order to yield the (meth)allyl-oxazolidine (VI). Examples of aldehydes and ketones which can be used for the intended purpose are isobutyric aldehyde, acetone, methyl-ethyl-ketone, cyclopentanone and cyclohexanone. Isobutyric aldehyde and methyl-ethyl-ketone are preferably used. The reaction is advantageously carried out at a temperature comprised within the range of from 20° to 100° C., in the absence of solvents, with the aldehyde or ketome being refluxed, so as to azeotropically remove water formed as a reaction byproduct. In this case, the process is carried out with an excess of from 20 to 100% of the aldehyde or ketone over the relevant stoichiometric amount.

According to an alternative route, the reaction is carried out in the presence of a solvent, of either aliphatic or aromatic type, capable of forming an azeotropic mixture with water. In this case, the process is carried out with a slight excess of the aldehyde or ketone over the stoichiometric amount thereof, and, in general, with an excess of from 5 to 20%. The reaction is moderately exothermic, and is complete within a time of from about 4 to 10 hours, as a function of the selected temperature. At the end of the reaction, the possibly used solvent and the excess of aldehyde or ketone are removed. On the contrary, a distillation of the N-(meth)allyl-oxazolidine is not necessary.

The (meth)allyl-oxazolidine (VI) is then reacted with the polymercaptan (VII) in order to yield the polyoxazolidine (I) according to the present invention. The reaction is carried out with stoichiometric, or quasi-stoichiometric, amounts of the reactants, by operating in bulk, or in the presence of solvents. In particular, the reaction proceeds easily at temperatures of the order of 50°–60° C., developing exothermic heat, desirably in the presence of a catalyst, normally selected from among the radicalic initiators, such as azobisisobutyronitrile, and similar compounds. The concentration of the catalyst can be comprised within the range of from 0.01 to 2%, and preferably within the range of from 0.1 to 0.5% by weight in the reaction medium. By operating under the above conditions, a time of about 6 hours makes it possible the reaction to be completed, or substantially completed, as it can be verified by detecting the disappearance of the allyl groups from the reaction mixture. As a practical matter of fact, said allyl groups should be reduced down to a value lower than 5% relatively to the initial value. In case a solvent is present, this latter is removed at the end of the reaction by means of vacuum evaporation. The reaction proceeds up to a practically quantitative yield. The so-produced polyoxazolidine (I) is a liquid with a viscosity value which is a function of the complexity of its molecular structure.

The polymercaptan (VII) can be obtained by means of the reaction of the diol or polyol (VIII) with a mercaptocarboxy acid (IX). The diols or polyols suitable for the intended purpose can be selected from among ethylene glycol, butanediol, hexanediol, neopentyl glycol, cyclohexanediol, cyclohexanedimethanol, pentaerythritol and trimethylolpropane.

The mercaptocarboxy acid is selected from among mercaptoacetic acid and mercaptopropionic acid. The reaction is preferably carried out by means of the direct esterification of the diol or polyol (VIII) with the stoichiometric, or quasi-stoichiometric, amount of the mercaptocarboxy acid (IX), under conditions of elimination of water formed as a reaction byproduct. The reaction requires in general the presence of a catalyst, which preferably is a strong acid, such as, e.g., p-toluenesulfonic acid.

According to the preferred procedure, the reaction is carried out in a hydrocarbon solvent (such as, e.g., toluene and xylene), with a concentration of catalyst comprised within the range of from 0.1 to 5% by weight in the reaction medium, at the solvent refluxing temperature (in general, at temperatures lower than 150° C., and typically comprised within the range of from about 80° to about 130° C.), so as to azeotropically remove the condensation water. The advantage afforded by the use of the above disclosed acidic catalysts consists in that they can be easily removed from the reaction medium, e.g., by using a base, such as calcium oxide. The reaction is continued until a low acidity number (<3 mg of KOH/g) is reached, and is ended when the theoretical amount of water has been developed. The time required for the reaction to be complete is of the order of from 10 to 12 hours. At the end of the reaction, the acidic catalyst is neutralized, the solution is filtered, the solvent is removed, and the polymercaptan (VII) is recovered. The reaction yield is practically quantitative.

The process for preparing the polyoxazolidines (I) according to the present invention shows several advantages. First of all, the values of yield and of selectivity of the concerned reactions are high. Furthermore, stable, easily handled intermediates are used; and catalysts are employed, which are not dangerous for polyisocyanates, with an easy addition of the polyoxazolidines according to the present invention to the isocyanate systems being hence possible without the pot stability of the compositions being in any way endangered. Finally, the process is flexible, in that it makes it possible a large number of polyoxazolidines to be produced, which display a very high degree of functionality, generally variable within the range of from 2 to 10.

The polyoxazolidines (I) according to the instant invention are products compatible with the most common classes of organic polymers, with the advantage that they are flowing liquids, with a rather low viscosity, generally lower than 100,000 cps at 25° C. The presence of sulfur in thioether form in the polyoxazolidines according to the instant invention supplies stability to photooxidation and a better resistance to oils to the manufactured articles to which they are added, and this is the greatest advantage thereof, as compared to the products known from the prior art.

The polyoxazolidines (I) according to the present invention constitute latent catalysts in that they immediately hydrolyze in the presence of moisture, also of room humidity, with the oxazolinic ring being cleft and polyalkanolamines being generated. They are therefore useful as crosslinking agents for polyisocyanates, polyepoxides and polyacrylates (Michael's addition), in compositions for coatings, sealant compositions and adhesive compositions. Such polyoxazolidines are particularly useful in combination with polyisocyanates in that, thanks to their intrinsic features, they do not endanger the useful life thereof, and can therefore be combined with said polyisocyanates to yield single-component systems which are fluid under room conditions, do not contain solvents, and crosslink in the presence of room humidity. The low viscosity values of the polyoxazolidines is particularly advantageous in these formulations.

The polyisocyanates useful for such formulations are those which can be obtained by starting from aliphatic and/or aromatic isocyanates and from organic, either difunctional, or polyfunctional, organic polymers of low molecular weight (i.e., with a molecular weight of the order of from 500 to 20,000), with a hydroxy functionality at their chain ends. Among these, the polyethers, polyesters, polycarbonates, polybutadienes as well as some hybrid polymers, such as hydroxy-capped copolyether polycarbonates and copolyester polycarbonates, can be cited.

Such polyisocyanates are formulated into compositions with the polyoxazolidines according to the present invention in such a way that two equivalents of isocyanate groups in the polyisocyanate correspond to each oxazolidinic equivalent in the polyoxazolidine. Deviations from this stoichiometry can be allowed, without the firmness of the crosslinked products being jeopardized to an excessive extent, provided that the polyoxazolidine is present in an amount comprised within the range of from 30% less, up to 10% more, relatively to the stoichiometric value.

The formulation containing polyisocyanates and polyoxazolidines can be prepared within a temperature range of from room temperature up to about 60° C., and is facilitated by the perfect compatibility of the two concerned species with each other. Catalysts suitable for accelerating the crosslinking can be contained in the formulation. Such catalysts are normally selected from among metal soaps, and in particular organometallic compounds of tin, and from among the organic acids, in particular p-toluenesulfonic acid and naphthoic acid. Besides the catalysts, other additives can be added to the formulations, such as organic or inorganic fillers, thixotropic agents, flame retardants, adhesion promoters, stabilizers. U.V. absorbers, the whole according to the normal practice.

The so obtained formulations undergo crosslinking with a good crosslinking speed, due to the effect of environmental humidity, yielding manufactured articles endowed with excellent general characteristics, in particular as far as the heat resistance, the chemical resistance and the resistance to ageing are concerned, and with a very good resistance to oxidation.

The following experimental examples are reported for the purpose of better illustrating the invention.

EXAMPLE 1

Preparation of Polymercaptans (a) Ethylene Glycol Dimercapto Propionate

Ethylene glycol (62.07 g, 1.0 mol), beta-mercaptopropionic acid (212.3 g, 2.0 mol), benzene (250 ml) and p-toluenesulfonic acid (4.0 g, 1.5% by weight) are charged to a flask equipped with a magnetic-bar stirrer, a Markuvson's head, a refluxing condenser and a nitrogen inlet. With the reaction mixture being kept efficaciously stirred, the flask is heated up to a temperature which causes the reaction mixture to vigorously reflux, which makes it possible the theoretical amount of condensation water to be collected by means of the Markuvson's head within a time of about 10 hours (36 ml, yield about 100%). To the solution in benzene, cooled down to room temperature, calcium oxide powder (50 g) is added, and the resulting mixture is stirred one hour at room temperature and is finally filtered through a layer of celite laid on a sintered glass filter. After washing of the filter with two aliquots of benzene of 30 ml each, benzene is removed from the solution by vacuum evaporation, and 237.1 g of ethylene glycol dimercaptopropionate is obtained (yield>99%), as a slightly blue-coloured liquid, having a specific gravity of 1.2 g/ml at 20° C., acid number<1 mg of KOH/g and molecular weight 238:

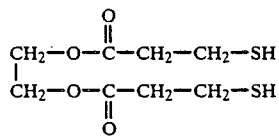

(b) Trimethylolpropane Trimercaptopropionate

By operating in the same way as disclosed under above (a) point, trimethylolpropane (67.09 g, 0.5 mol) and beta-mercaptopropionic acid (159.2 g, 1.5 mol) are reacted with each other in order to produce trimethylolpropane trimercaptopropionate with a nearly quantitative yield (198 g, yield 100%), with an acid number of <1 mg of KOH/g, a density 1.19 and a molecular weight of 398:

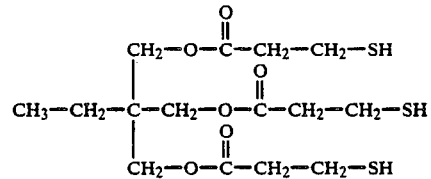

EXAMPLE 2

Preparation of N-allyl-ethanol-amine

Allyl-amine (285 g, 5.0 mol) is charged, under a nitrogen blanketing atmosphere, to an autoclave of 1 liter of capacity, and then ethylene oxide (110 g, 2.5 mol) is added to the autoclave within a 1-hour tine. At the end of this time period the reaction mixture is cooled and submitted to rectification under a pressure of 12 torr, in order to separate unreacted allyl-amine and N-allyl-ethanolamine. This latter is collected at 75°-78° C. in an amount of 202 g (2.0 mol), with a yield of 80% relatively to ethylene oxide. Molecular weight 101, purity>99% at gas-chromatography.

EXAMPLE 3

Preparation of-N-allyl-oxazolidine

N-allyl-ethanolamine (50.5 g, 0.5 mol) and benzene (250 ml) are charged, under a nitrogen blanketing atmosphere, to a flask of 1 liter of capacity equipped with a magnetic-bar stirrer, a Markuvson's head, a refluxing condenser and a thermometer. Isobutyraldehyde (93.6 g, 1.3 mol) is then gradually added, taking care of not exceeding the temperature of 50° C. inside the flask. At the end of the addition, the flask is dipped in a heating bath and its content is kept under refluxing conditions for 12 hours, with the condensation water (18 g, 1 mol) being collected by azeotropic distillation. The evaporation of the solvent at 20° C. and under a residual pressure of 10 torr (under nitrogen) produces N-allyl-oxazolidine (77 g, 0.5 mol, yield 100%, molecular weight 155) having the following structure:

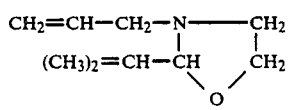

EXAMPLE 4

Preparation of Polyoxazolidine 2-S

The ethyleneglycol dimercaptopropionate of Example 1(a) (79 g, 0.33 mol) and the N-allyl-oxazolidine of Example 3 (155 g, 1.0 mol) is charged, under a nitrogen atmosphere to a flask equipped with a mechanical blade stirrer, together with azobisisobutyronitrile (2.0 g, 0.85% by weight). The flask is dipped in an oil bath at 50° C. and the reaction mass is kept stirred. An exothermic reaction starts, which increases the inner temperature up to 75° C. after about 30 minutes of reaction. When the development of exothermic heat ends, the temperature in the flask is increased up to 60° C. and is kept at this value for the successive 6 hours. A polyoxazolidine (234 g) is obtained with a practically quantitative yield, as a yellow liquid (specific gravity 1.04 g/ml, viscosity 900 cps at 25° C.), with a molecular weight of 548, which can be represented by means of the formula:

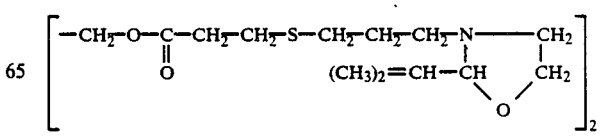

EXAMPLE 5

Preparation of Polyoxazolidine 3-S

By operating in the same way as of Example 4, a polyoxazolidine is prepared by starting from the N-allyl-oxazolidine of Example 3 (207 g, 1.33 mol) and from the trimethylolpropane trimercaptopropionate of Example 1(b) (177 g, 0.445 mol), in the presence of 2.0 g (0.52% by weight) of azobisisobutyronitrile. 384 g is obtained (yield about 100%) of slightly-yellow-coloured, liquid polyoxazolidine (specific gravity 1.02 g/ml, viscosity 1,500 cps at 25° C.), with a molecular weight of 863, which can be represented by means of the formula:

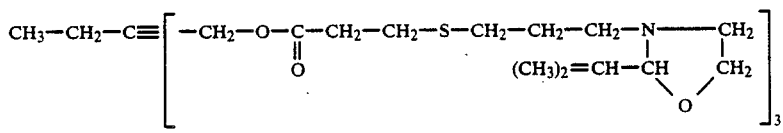

EXAMPLE 6

An aliphatic polycarbonate with hydroxy-capped chains (a commercial product RAVECARB 107, manufactured by Enichem, with a number average molecular weight of 1850, and a viscosity of 8000 cps at 25° C.) (92.5 g, 50 mmol) and isophoronediisocyanate (33.3 g, 150 mmol) are reacted at 75° C. until the total disappearance of the hydroxy groups, by operating under a nitrogen atmosphere, in a flask equipped with a mechanical blade stirrer and a thermometer. The resulting NCO-capped prepolymer is cooled down to 50° C. and at this temperature xylene (20 ml), naphthoic acid (0.3 g), dibutyl-tin dilaurate (30 mg) and the polyoxazolidine 3-S of Example 5 (20 g, 23.2 mol) are added. After homogenization and degassing, the product is poured on aluminum plates, with a layer of product of 2 mm of thickness being produced, and is crosslinked under room conditions. The skin time results to be of approximately 60 minutes. After a 30-days crosslinking time at room temperature, the following characteristics are determined:
absence of bubbles in the manufactured article;
gel: 87%;
hardness (Shore A): 67;
tensile strength: 19.8 N/mm$^2$;
deformation: 950%
Young's secant modulus (0.01 kN): 29.3 N/mm$^2$;
water absorption: 1.32% by weight;
weight loss (in water): 0.94% by weight:
oil absorption: −2.8% by weight;
(end Shore A hardness=88).

After 400 hours of exposure in WOM, the material, without any stabilizers added, shows the following characteristics:
hardness (Shore A): 83;
tensile strength: 37 N/mm$^2$;
deformation: 1010%
Young's secant modulus (0.01 kN): 38.5 N/mm$^2$;

After 600 hours of immersion in water at 50° C., the material shows the following characteristics:
hardness (Shore A): 85;
tensile strength: 39 N/mm$^2$;
deformation: 1100%
Young's secant modulus (0.01 kN): 34 N/mm$^2$;

After 600 hours of ageing in an oven at 120° C. in atmospheric air, the material shows the following characteristics:
hardness (Shore A): 87;
tensile strength: 38 N/mm$^2$;
deformation: 1050%
Young's secant modulus (0.01 kN): 28 N/mm$^2$;

EXAMPLE 7

Example 6 is repeated with the only exception that polyoxazolidine 3-S is used in an amount of 17.5 g (20.3 mmol). After a 30-days crosslinking at room temperature, the following characteristics are determined:
skin time: about 60 minutes,
the manufactured article contains some bubbles, due to a slight release of carbon dioxide;
hardness (Shore A): 72;
gel: 94%;
tensile strength: 22.8 N/mm$^2$;
deformation: 990%
Young's secant modulus (0.01 kN): 48 N/mm$^2$;
water absorption: 1.17% by weight;
weight loss (in water): 0.78% by weight:
oil absorption: −3.8% by weight;
(end Shore A hardness=86).

After 400 hours of exposure in WOM, the material shows the following characteristics:
hardness (Shore A): 86;
tensile strength: 40 N/mm$^2$;
deformation: 1150%
Young's secant modulus (0.01 kN): 23 N/mm$^2$;

After 600 hours of immersion in water at 50° C., the material shows the following characteristics:
hardness (Shore A): 85;
tensile strength: 36 N/mm$^2$;
deformation: 1100%
Young's secant modulus (0.01 kN): 22 N/mm$^2$;

After 600 hours of ageing in an oven at 120° C. in atmospheric air, the material shows the following characteristics:
hardness (Shore A): 85;
tensile strength: 38 N/mm$^2$;
deformation: 950%
Young's secant modulus (0.01 kN): 26 N/mm$^2$;

EXAMPLE 8

The same polycarbonate as used in Example 6 (92.5 g; 50 mmol) is combined with toluene diisocyanate (179 g; 102 mmol) until the disappearance of the hydroxy groups, by operating at 75° C., for about 7 hours. The product is then added at 50° C. to the polyoxazolidine of Example 5 (14.4 g; 13.9 mmol) and the resulting mixture is diluted with 20 ml of xylene. The product is caused to crosslink and the following characteristics are determined:
skin time: about 60 minutes,
absence of bubbles in the manufactured article;
gel: 89%;
hardness (Shore A): 52;
tensile strength: 7.5 N/mm$^2$;

deformation: 900%
Young's secant modulus (0.01 kN): 1.2 N/mm$^2$;
water absorption: 1.3% by weight;
weight loss (in water): 0.7% by weight:
oil absorption: −2.05% by weight;

EXAMPLE 9

The test of Example 8 is repeated, with toluene-diisocyanate being replaced by isophorone-diisocyanate (22.9 g; 103 mmol). After coupling with the diisocyanate, the polyoxazolidine of Example 5 (13.5 g; 15.6 mmol), naphthoic acid (0.3 g), dibutyltin dilaurate (0.02 g) and xylene (20 ml) are added to the resultant NCO terminated prepolymer. After being homogenized at 50° C., the product is caused to crosslink under room conditions, in order to yield a hardened product having the following characteristics:
absence of bubbles in the manufactured article;
gel: 75%;
hardness (Shore A): 50;
tensile strength: 3.80 N/mm$^2$;
deformation: 930%
Young's secant modulus (0.01 kN): 1.9 N/mm$^2$;
water absorption: 1.42% by weight;
weight loss (in water): 0.7% by weight:
oil absorption: −0.4% by weight;

EXAMPLE 10

A commercial polytetrahydrofuran (TERECOL by Du Pont Company; hydroxy number 56) (100 g; 50 mmol) is reacted with isophorone-diisocyanate (22.9 g; 103 mmol) for 6 hours at 75° C., until the disappearance of the hydroxy groups. At the temperature of 50° C., the polyoxazolidine of Example 5 (14.5 g; 16.8 mmol), naphthoic acid (0.3 g), dibutyltin dilaurate (0.03 g) and xylene (20 ml) are added to the thus obtained product.

After being homogenized, the product is caused to crosslink under room conditions, in order to yield a hardened product having the following characteristics:
gel: 76.8%;
hardness (Shore A): 40;
tensile strength: 8.2 N/mm$^2$;
deformation: 1150%
Young's secant modulus (0.01 kN): 8.0 N/mm$^2$;
water absorption: 2.7% by weight;
weight loss (in water): 1.2% by weight:
oil absorption: +8.3% by weight;

EXAMPLE 11

Trimethylol-propane (0.8 g, 6 mmol) is reacted with isophorone-diisocyanate (22.2 g, 100 mmol) at 75° C., for 1 hour, with stirring. To the so obtained adduct, the commercial polycarbonate-diol of Example 6 is added (75.8 g, 41 mmol) and the reaction is continued at 75° C. until the disappearance of the hydroxy groups (as determined by means of I.R. spectroscopy), for which about 6 hours are necessary. The reaction product is diluted at 50° C. with xylene (15 ml) and then dibutyltin dilaurate (300 ppm), naphthoic acid (0.2 g), and polyoxazolidine 2-S of Example 4 (15 g, 27.6 mol) are added to it.

After homogenization, the product is poured on aluminum plates, with a layer of 2 mm of thickness being formed, and is allowed to crosslink in the presence of environmental humidity for 30 days at room temperature.

The following characteristics are determined:
skin time: 20 minutes;
absence of bubbles in the manufactured article;
gel: 75%;
hardness (Shore A): 42;
tensile strength: 9.1 N/mm$^2$;
deformation: 1050%
Young's secant modulus (0.01 kN): 5.7 N/mm$^2$;

In the tests reported in the preceding experimental examples:
the tensile tests were carried out in compliance with ASTM standard tests;
the values of water absorption, and the weight loss in water were evaluated on samples kept dipped for 70 hours in demineralized water at room temperature;
the value of oil absorption was evaluated on samples kept dipped for 48 hours in vaseline oil at 80° C.;
the measurement of the gel was carried out on samples kept dipped in methylene chloride for 48 hours at room temperature;
the measurements in WOM (Weather-O-Meter) were carried out with continuous light cycles, by means of an ageing xenon lamp of 6500 W of power, U.V. irradiance of 0.33 W/m$^2$, samples on revolving carrousel, constant temperature (60° C.), black background and constant humidity (relative humidity 50%).

I claim:

1. Polyoxazolidines which can be defined by means of the general formula:

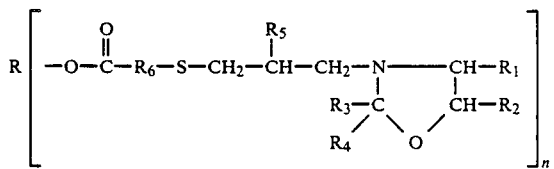

wherein:
R is an alkylenic radical containing from 2 to 12 carbon atoms, or a cycloalkylenic radical;
$R_1$ and $R_2$, which can be either equal to, or different from, each other, represent the hydrogen atom, an alkyl radical with a straight or branched chain, containing from 1 to 6 carbon atoms, or an aryl radical;
$R_3$ and $R_4$, which can be either equal to, or different from, each other, represent the hydrogen atom, an alkyl radical with a straight or branched chain, containing from 1 to 6 carbon atoms, a cycloalkyl radical, or an aryl radical;
$R_5$ represents the hydrogen atom or the methyl radical;
$R_6$ represents the methylene or ethylidene radical;
n represent an integer comprised within the range of from 2 to 10.

2. Polyoxazolidines according to claim 1, characterized in that
R is an alkylenic radical containing from 2 to 6 carbon atoms;
$R_1$ and $R_2$ represent the hydrogen atom; $R_3$ and $R_4$ represent, independently from each other, an alkyl radical with a straight or branched chain, containing from 1 to 4 carbon atoms; or either of $R_3$ and $R_4$ represents a hydrogen atom, and the other one represents an alkyl radical with a straight or branched chain, containing from 1 to 4 carbon atoms;

$R_5$ represents the hydrogen atom or the methyl radical;

$R_6$ represents the methylene radical or the ethylidene radical; and n represent an integer comprised within the range of from 2 to 6.

3. Process for preparing the polyoxazolidines according to claim 1, characterized in that:

a (meth)allyl-amine (II):

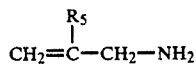

is reacted with an alkylene oxide (III):

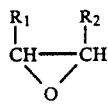

in order to yield an N-(meth)allylalkanolamine (IV):

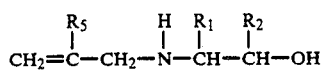

said meth(allyl)alkanolamine (IV) is reacted with an aldehyde or a ketone (V):

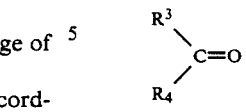

in order to yield a meth(allyl)oxazolidine (VI):

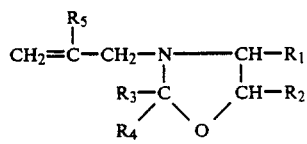

said (meth)allyl-oxazolidine (VI) is reacted with a polymercaptan (VII):

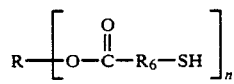

in order to yield the polyoxazolidine (I);

wherein R, $R_1$, $R_2$, $R_3$, $R_4$, $R_5$, $R_6$ and n have the same meaning as specified in claims 1 or 2.

* * * * *